(12) United States Patent
Chen et al.

(10) Patent No.: US 6,980,857 B2
(45) Date of Patent: Dec. 27, 2005

(54) PATIENT CONTROLLED ATRIAL SHOCK THERAPY

(75) Inventors: Victor T. Chen, Minnetrista, MN (US); Gary T. Seim, Minneapolis, MN (US); Hal Propp, Oakdale, MN (US); LeAnne Eberle, St. Louis Park, MN (US); Lynn TeWinkel, Minnetonka, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 549 days.

(21) Appl. No.: 09/839,122

(22) Filed: Apr. 20, 2001

(65) Prior Publication Data

US 2002/0156504 A1 Oct. 24, 2002

(51) Int. Cl.⁷ .................................. A61N 1/18
(52) U.S. Cl. .............................. 607/5; 607/32; 607/60
(58) Field of Search ......... 607/5, 32, 60; 600/515–518

(56) References Cited

U.S. PATENT DOCUMENTS

| | | | |
|---|---|---|---|
| 3,952,750 A | 4/1976 | Mirowski et al. | |
| 5,311,449 A | 5/1994 | Adams | |
| 5,336,245 A | 8/1994 | Adams Theodore P. et al. | |
| 5,342,408 A | 8/1994 | deCoriolis et al. | |
| 5,464,431 A | 11/1995 | Adams et al. | |
| 5,490,862 A | 2/1996 | Adams et al. | |
| 5,518,001 A | 5/1996 | Snell | |
| 5,662,689 A | 9/1997 | Elsberry et al. | 607/5 |
| 5,674,249 A | 10/1997 | de Coriolis et al. | |
| 5,755,737 A | 5/1998 | Prieve et al. | |
| 5,775,737 A | 7/1998 | Morgner et al. | 285/49 |
| 5,836,975 A | 11/1998 | DeGroot | 607/5 |
| 5,999,851 A | 12/1999 | White | |
| 6,016,442 A * | 1/2000 | Hsu et al. | 600/518 |
| 6,068,651 A | 5/2000 | Brandell | |
| 6,618,617 B2 | 9/2003 | Favet et al. | 607/5 |
| 6,718,198 B2 * | 4/2004 | Conley et al. | 600/523 |
| 2004/0034389 A1 | 2/2004 | Chen et al. | 607/5 |

OTHER PUBLICATIONS

Medtronic, Jewel AF Model 7250 System Reference Guide, 1997, Minneapolis, Minnesota. Especially pp. 3-11-3-12, 7-11-7-13.

* cited by examiner

*Primary Examiner*—Mark Bockelman
(74) *Attorney, Agent, or Firm*—Schwegman, Lundberg, Woessner & Kluth, P.A.

(57) ABSTRACT

An implanted cardiac device detects an atrial arrhythmia and provides periodically updated atrial arrhythmia status as long as the arrhythmia is ongoing. A patient may request an indication of ongoing atrial arrhythmia status from external to the patient using a patient activator. The patient activator may include a magnet for closing a reed switch in the implanted device to provide the request or may provide the request over a telemetry link to the implanted device. The implanted device may provide the requested atrial arrhythmia status and other information in the form of an audible tone produced by the implanted device or as a message telemetered from the implanted device to the patient activator. The patient activator may include a tone detector and display for providing a visual indication of the atrial arrhythmia status indication. The magnet activator may also be employed to request or withhold atrial shock therapy.

21 Claims, 3 Drawing Sheets

PATIENT CONTROLLED ATRIAL SHOCK THERAPY

FIELD OF THE INVENTION

The present invention pertains generally to medical devices and more particularly to implantable medical devices such as devices for monitoring activity of the heart and providing electrical shock therapy thereto including automatic implantable cardioverter defibrillator devices for treating atrial arrhythmias and external patient operable devices for monitoring and controlling the operation of such implantable medical devices.

BACKGROUND OF THE INVENTION

Various types of medical devices are employed to monitor electrical or other activity of the heart and to provide therapy to the heart in response to the detection of irregular cardiac rhythms. Such devices may be implantable beneath the skin of a patient, i.e., in the patient's chest. Such implantable devices include a hermetically sealed canister containing electronic circuitry for implementing the functions of the device, one or more electrodes implanted in one or more of the chambers of the heart, or in close proximity thereto, and leads for connecting the electrodes to the circuitry within the device canister. The device circuitry includes circuitry for detecting electrical signals produced by the heart, which signals are picked up at the electrodes, along with circuitry, typically implemented in a microprocessor, for analyzing the thus-detected cardiac signals. The device may also include circuitry for providing therapy in the form of electric shock signals applied to the heart. Such signals are provided to the heart, via the leads and electrodes mounted in the heart, in response to the detection of an irregular cardiac rhythm by the analysis circuitry based on the detected cardiac activity signals. The implantable device may also include a transmitter/receiver, for transmitting cardiac activity and other information to an external device for, e.g., storage and/or further analysis, and for receiving information, such as programming instructions, from the external device via, for example, an RF link.

An example of such an implantable cardiac device is an automatic implantable cardioverter defibrillator (AICD) for treating atrial arrhythmias, e.g., atrial tachycardia, fibrillation, flutter, etc. (The functionality of an atrial AICD may be combined with those of a bradycardia pacemaker, ventricular defibrillator, etc.) Atrial arrhythmias are probably the most common cardiac arrhythmia. Although atrial arrhythmias are not usually life-threatening, patients with atrial arrhythmias generally experience palpitations of the heart, and may experience dizziness or even loss of consciousness. Atrial arrhythmias, such as atrial fibrillation, also have been associated with strokes and other conditions. Atrial arrhythmias can occur suddenly. Implantable atrial cardioverter defibrillators are programmed to detect the onset of atrial arrhythmias and to provide an appropriate electrical shock therapy to the atria to terminate the atrial arrhythmia. The atrial shock therapy to be provided may depend upon the type of atrial arrhythmia detected, e.g., atrial tachycardia versus atrial fibrillation. Shock therapy provided by an implantable atrial cardioverter defibrillator may include a relatively high voltage level atrial defibrillation or cardioversion pulse, which is typically delivered to the atria in synchronism with a detected or paced ventricular activation, to terminate atrial fibrillation or flutter. Atrial antitachycardia pacing may be applied by the implantable device to terminate atrial tachycardia. Atrial antitachycardia pacing typically involves a train of pacing pulses applied to the atria at a rate slightly higher than the rate of the tachycardia.

Various systems and methods have been developed to allow patients having implanted atrial cardioverter defibrillators to monitor and control, to at least some degree, operation of the implanted device. For example, U.S. Pat. No. 5,490,862 describes an implantable atrial defibrillator which may be programmed to operate in a patient activated mode of operation. In the patient activated mode, an atrial fibrillation intervention sequence is performed by the implanted device in response to the receipt of a sequence command generated from external to the patient. The sequence command may be generated, for example, by an external magnet applied by the patient to near the implantation site, to close and then open a reed switch mounted in the implanted device and coupled to the device microprocessor. The intervention sequence thus initiated by the patient, when he believes he is experiencing an atrial arrhythmia, includes atrial fibrillation detection by the implanted device and, if atrial fibrillation is confirmed, the application of cardioverting electrical energy to the atria.

U.S. Pat. No. 5,674,249 describes the use of a portable communication device which allows a patient to monitor and control the operation of an implanted atrial defibrillator. The portable communication device, which may be dimensioned to be hand held by a patient, includes a transmitter/receiver for communicating with the implanted device via a telemetry (e.g., RF) link. In this system, an atrial fibrillation intervention sequence may be initiated in an implanted device in response to a sequence command generated from the portable communication device. The patient may also use the portable communication device to program the implanted device into an automatic mode wherein the intervention sequence is initiated automatically at predetermined times. The handheld portable communication device receives an acknowledgment signal from the implanted device when a command signal sent from the communication device is received by the implanted device. The receipt of the acknowledgment signal by the portable handheld communication device is displayed to the patient on the device. The display includes a description of the task being performed by the implanted device in response to the command signal sent by the patient. Thus, a patient is able to both monitor and control operation of an implanted cardiac device to some degree.

U.S. Pat. No. 5,999,851 describes an implantable atrial defibrillator which includes an atrial fibrillation detection only mode of operation. In this mode, atrial fibrillation detection is initiated in the implanted device by a command signal sent from an external patient operated communication device, which is in communication with the implanted defibrillator via a telemetry (e.g., RF) link. If atrial fibrillation is detected by the implanted atrial defibrillator, an appropriate signal is communicated to the patient operated communication device, and a visual and/or audible message is provided by the communication device to the patient to indicate whether or not atrial fibrillation is detected. In this detection only mode, a further signal must be provided from the communication device to the implanted device to initiate cardioversion therapy, preferably after continued atrial fibrillation is confirmed by the implanted device.

In each of the systems described above, atrial fibrillation detection, or atrial fibrillation detection followed by atrial shock therapy, if required, may be initiated by a patient using an external communication device. To monitor the progress of an ongoing atrial arrhythmia event in such systems, a patient must repeatedly signal the implanted device to reinitiate atrial fibrillation detection. Furthermore, to both monitor the status of an atrial arrhythmia detected by the implanted device and control the providing of shock therapy to the atria by the implanted device a relatively complicated external communication device employing a telemetry link is used to provide a variety of control signals from the communication device to the implanted device.

What is desired is an atrial shock therapy system which allows a patient to monitor the status of an ongoing atrial arrhythmia event without requiring repeated reinitiation by the patient of atrial arrhythmia detection. Preferably, a relatively simple and inexpensive patient controlled activator or communication device may be employed by the patient both to monitor atrial event status as determined by an implanted device as well as to control the providing of atrial shock therapy by the implanted device.

SUMMARY OF THE INVENTION

The present invention provides a system and method which allows a patient with an implanted automatic implantable cardioverter defibrillator to monitor the status of an atrial arrhythmia detected by the implanted device and to control the providing of shock therapy to the atria by the device. In accordance with the present invention, a patient employs an external activator communication device to request an indication of the status of an ongoing atrial arrhythmia event without requiring repeated initiation of atrial event detection by the implanted device. The patient activator communication device may preferably be implemented in a relatively simple and inexpensive manner and allow the patient both to request atrial arrhythmia event status as well as to control the providing of electrical shock therapy to the atria by the implanted device to terminate an atrial arrhythmia event.

The present invention may be implemented in an implantable cardiac device, such as an automatic implantable cardioverter defibrillator, which provides atrial arrhythmia detection and electrical shock therapy to the atria to terminate such atrial arrhythmias. (The implantable device may also include ventricular arrhythmia monitoring and ventricular shock therapy functionality and/or ventricular pacing functionality, as well as atrial pacing capability.) The implantable cardiac device includes signal detection circuitry, connected via leads to electrodes positioned in the atria and, preferably, the ventricles of the heart, to detect electrical heart activity signals. An implanted device system processor monitors the output provided by the signal detection circuitry to detect the occurrence of an atrial arrhythmia, e.g., atrial tachycardia, fibrillation, and/or flutter, using known atrial arrhythmia detection algorithms. The implantable device includes cardioverter/defibrillator circuitry, controlled by the device processor, for providing defibrillation shock therapy, and/or antitachycardia pacing, depending upon the type of atrial arrhythmia identified, to the atria via the leads and electrodes implanted in the heart. The implantable device is preferably also provided with a telemetry receiver/transmitter, coupled to the device processor, to allow the processor to transmit cardiac activity and other data to an external programmer device for storage and/or further analysis, and to receive data, such as programming instructions, from the external programmer device. The external programmer device is a relatively complicated device used by a physician to program the implanted device and query cardiac activity data therefrom.

In accordance with the present invention, a patient, having an implanted cardiac device in accordance with the present invention, is able to monitor an atrial arrhythmia detected by the implanted device and control the providing of atrial shock therapy by the implanted device using a patient activator communication device. The patient activator is preferably a relatively small, handheld device, which allows the patient to initiate a patient activation operation in the implantable device to determine the status of an atrial arrhythmia event detected by the implanted device (if any) as well as, preferably, to control the providing of shock therapy to the atria by the implantable device to terminate the atrial arrhythmia event. The patient activator preferably employs a relatively simple mechanism for initiating a patient activation operation. For example, the patient activator may include a magnet which, when placed near the implantation site of the implanted device, operates a reed switch in the implanted device, which is coupled to the implanted device processor, thereby to initiate a patient activation operation.

In response to the receipt of a patient activation request, the implanted device provides information indicating the status of any ongoing atrial arrhythmia detected thereby to the patient. For example, the implanted device may include a tone-producing circuit, for driving a small speaker, which produces distinctive tones, audible to the patient, which indicate that the implanted device has received the patient activation request and whether or not an atrial arrhythmia is ongoing. The implanted device continually monitors and updates the status of an ongoing atrial arrhythmia event. Periodically, e.g., every ventricular cycle, the implanted device updates the tone, or other signal, produced by the implanted device, to indicate to a patient any change in the status of the atrial arrhythmia event, as long as the patient activation request is provided by the activator. Thus, information on the changing status of an atrial arrhythmia event is provided periodically to a patient, e.g., as long as the patient activator is positioned near the implantation site. In accordance with the present invention, a patient is not required to reinitiate periodically atrial arrhythmia detection by the implanted device in order to obtain current atrial arrhythmia event status information.

The implanted device may also provide other information to the patient, such as the availability of the implanted device to provide atrial shock therapy, in response to the initiation of an activation request by the patient using the patient activator. For example, different audible tones may be produced by the implanted device depending on both whether or not an atrial arrhythmia event is occurring and/or whether or not atrial shock therapy is available.

The patient activator communication device may also provide a visual indication to the patient indicating the ongoing status of an atrial arrhythmia event and/or the availability of atrial shock therapy. For example, the patient activator device may include tone detection circuitry which detects the various tones produced by the implanted device in response to a patient initiated activation request. The tone detection circuitry converts such tones into electrical signals, which may be analyzed by an activator processor, which, in turn, drives a display (e.g., an LED or lamp display) on the activator to provide a periodically updated visual indication of atrial arrhythmia event status and/or atrial shock therapy availability (as long as a patient activation request is provided from the activator to the implanted device).

The patient activator communication device may also be employed to control the providing of atrial shock therapy by the implanted device. For example, a patient activation operation, as described above, may be initiated by positioning the patient activator device magnet near the implantable device implant site for at least a relatively short initial duration (e.g., one second). In response to the presence of the patient activator device, the implantable device provides an indication to the patient (e.g., audibly) of the status of any detected atrial arrhythmia event. If the patient activator device is removed from near the implantation site shortly thereafter (i.e., within less than a threshold duration, e.g., seven seconds, from initial application of the activator to the implantation site), atrial shock therapy will be withheld (i.e., disabled), and no atrial shock therapy will be provided even though an atrial arrhythmia has been detected and atrial shock therapy is otherwise available. However, if the patient activation operation is maintained for a longer period (e.g., more than the threshold duration), e.g., by maintaining the patient activator device magnet in position for more than the threshold duration, appropriate shock therapy (e.g., synchronized cardioversion and/or antitachycardia pacing, depending upon the nature of the atrial arrhythmia) will be requested and provided by the implantable device, e.g., after the patient activator is removed from the implant site. If the patient activation operation is maintained for an even longer period (e.g., longer than a stop therapy threshold duration, which may be, for example, sixty seconds), e.g., by maintaining the patient activator device magnet in position for longer than the stop therapy threshold duration, any shock therapy initiated in the implantable device may be disabled (until the patient activator is removed from position near the implant site and then replaced in position near the implant site for at least the initial duration to re-initiate a patient activation operation). Thus, a patient is able to employ a relatively simple and inexpensively implemented patient activator (e.g., a magnet) to both monitor atrial arrhythmia event status as detected by an implanted device as well as to control the providing of shock therapy to the atria by the implanted device to terminate the detected atrial arrhythmia event. In more general terms, in accordance with the present invention, the presence of a patient activation request may be used to request an atrial arrhythmia event status indication from an implanted device, while the duration of the same request signal is used to control the providing of atrial shock therapy by the implanted device.

Although a relatively simple and inexpensive patient activator device, e.g., including a magnet, tone detector circuitry, a processor, and a status display, may be employed in accordance with the present invention, a more complicated patient activator may also be used. A more complicated patient activator communication device may include a receiver/transmitter for communicating control signals to and receiving status information signals from the implanted cardiac device via a telemetry (e.g., RF) link with a corresponding receiver/transmitter in the implanted device. Such a patient activator communication device may include a patient input circuit, including buttons, switches, etc., for allowing a patient to signal via the telemetry link from the activator to the implanted device to initiate a patient activation operation. Atrial arrhythmia event status information may be communicated, in response to receipt of the activation request by the implanted device, from the implanted device to the activator over the telemetry link. Such status information may be displayed or otherwise presented in visual or audible form to the patient by the activator device. The patient activator may also employ telemetry to request and receive status information from the implanted device regarding the availability of atrial shock therapy, as well as to control the providing of atrial shock therapy by the implanted device.

Further objects, features, and advantages of the invention will be apparent from the following detailed description taken in conjunction with the accompanying drawings.

DETAILED DESCRIPTION OF THE PREFERRED EMBODIMENTS

Figure 1:
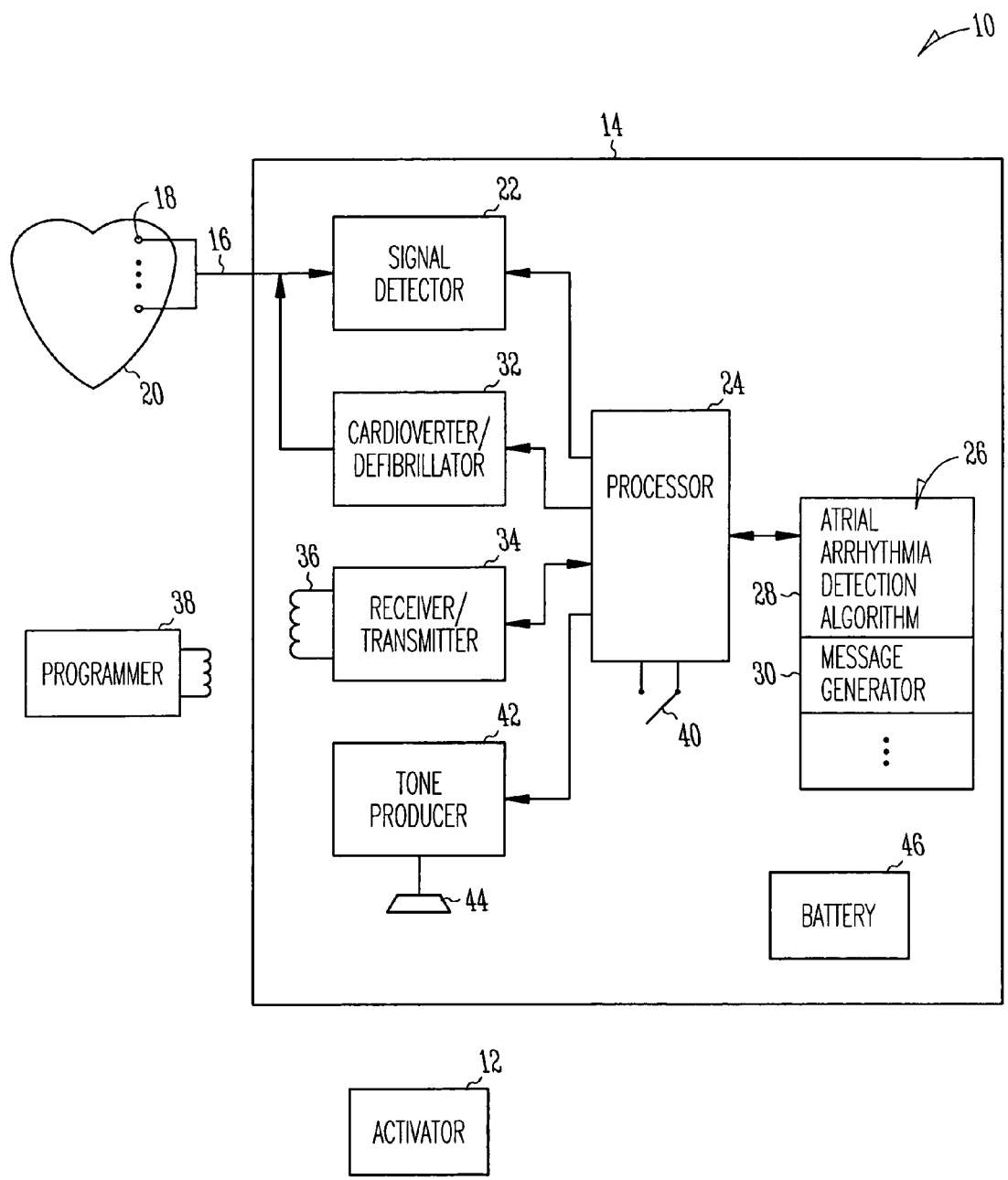
FIG. 1 is a schematic block diagram of an exemplary implantable cardiac device for detecting atrial arrhythmias and providing electrical shock therapy to the atria, and a patient activator communication device for controlling the implantable device to provide atrial arrhythmia event status information to the patient and to control the providing of shock therapy to the atria by the implantable device.

An exemplary implantable cardiac device 10 which may be controlled by a patient activator communication device 12 to provide atrial arrhythmia event status and other information to a patient and to provide patient controlled atrial shock therapy in accordance with the present invention is illustrated in, and will be described in detail with reference to, FIG. 1. Although described in detail herein with reference to an implantable device 10 having the primary function of detecting and treating atrial arrhythmias, it should be understood that the present invention may be employed with an implantable device which also performs other functions, such as ventricular monitoring and therapy and single or dual chamber bradycardia pacing.

The implantable cardiac device 10 includes a hermetically sealed canister 14 which encloses circuitry for detecting and analyzing cardiac arrhythmias and for providing electrical shock therapy to treat such arrhythmias. The circuitry within the canister 14 is connected via one or more leads 16 to one or more electrodes 18 which are implanted in or near the chambers of a patient's heart 20. The electrodes 18 pick up electrical signals produced in the chambers of the heart 20 and provide electrical contact for electrical pulses or shocks which are delivered to the chambers of the heart 20 to pace or defibrillate/cardiovert the heart 20. Depending upon the specific applications and functionality of the implantable cardiac device 10, electrodes 18 may be positioned in or near the atria, ventricles, or, preferably, both the atria and ventricles of the heart 20. In an implantable cardiac device 10 in accordance with the present invention for detecting atrial arrhythmias, and providing atrial shock therapy to terminate such atrial arrhythmias, for example, electrodes 18 are positioned in or near the atria, for detecting atrial activity and providing atrial shock therapy to the atria, as well as in the ventricles, for detecting ventricular activity, e.g., for use in verifying the presence of atrial arrhythmias and in synchronizing the providing of atrial cardioversion shock pulses to the atria with ventricular events. A plurality of leads 16 may be required to connect the electrodes 18 positioned in the heart 20 to the circuitry within the device canister 14. As is known in the art, multiple electrodes 18 may be coupled to the circuitry within the canister 14 via a single one of the leads 16. The canister 14, leads 16, and electrodes 18 are preferably designed such that the entire device 10 is implantable beneath the skin of a patient.

The leads 16 connect the electrodes 18 positioned within the heart 20 to signal detection circuitry 22 within the implantable device canister 14. The signal detection circuitry 22 may be implemented in a conventional manner to provide atrial and/or ventricular activity signals based on the cardiac signals picked up at the electrodes 18. Conventional signal detection circuitry 22 may include signal amplifiers and filters, and may include, in addition, circuitry for detecting atrial and ventricular depolarizations and for providing atrial and ventricular depolarization detection indication signals in response thereto, along with circuitry for obtaining electrogram signals and for providing digitized electrograms from the cardiac signals detected at the electrodes 18.

The signals provided by the signal detection circuitry 22 are provided to an implantable device system processor 24. The system processor 24 may be implemented, for example, as one or more conventional microprocessors with associated memory 26. Memory 26 may be an integral part of, or separated from, but coupled to, the processor 24. Memory 26 is employed in a conventional manner to store data, such as cardiac activity data, for analysis by the processor 24, as well as to store the programming instructions which control the functions performed by the processor 24. For example, programming instructions for implementing an atrial arrhythmia detection algorithm 28 by the processor 24, and for operating the processor 24 to generate messages 30 indicative of the status of an atrial arrhythmia event detected by the implanted device 10, the availability of atrial shock therapy, etc., may be stored in memory 26. These functions will be described in more detail below. Of course, other general and conventional programming instructions for the processor 24 may also be stored in memory 26.

The implantable cardiac device 10 also includes conventional cardioverter/defibrillator circuitry 32 for applying electrical energy to the heart 20 via the leads 16 and electrodes 18 positioned in the heart. In response to the detection of an atrial arrhythmia by the processor 24, based on cardiac signals provided by the signal detector 22, the processor 24 controls the cardioverter/defibrillator to provide electrical shock therapy to the heart 20 to terminate the atrial arrhythmia event. The type of electrical shock therapy provided to the heart 20 may depend upon the type of atrial arrhythmia event identified. For example, the cardioverter/defibrillator circuitry 32 may be controlled by the processor 24 to provide a relatively high voltage level atrial defibrillation pulse to the atria of the heart 20 to terminate an atrial fibrillation or flutter event. Such relatively high voltage shock therapy is preferably provided in synchronism with a detected or paced ventricular event, in order to prevent the atrial shock therapy from initiating a more serious ventricular arrhythmia. In response to the detection of a high-rate, but more regular, atrial arrhythmia, e.g., atrial tachycardia, the processor 24 may control the cardioverter/defibrillator circuitry 32 to provide atrial antitachycardia pacing to the atria to terminate the atrial arrhythmia event. Atrial antitachycardia pacing may typically include a rapid series of atrial pacing pulses delivered to the atria via a pacing lead 16 and one or more electrodes 18 positioned in or near the atria of the heart 20. Various atrial shock therapies are known to those skilled in the art, and will not be described in further detail herein.

The implantable device 10 may include receiver/transmitter circuitry 34 including an antenna coil 36. The receiver/transmitter 34 may be implemented in a conventional manner to transmit data from the system processor 24 out of the implanted device 10 to a remote programmer device 38. For example, cardiac activity data detected by the signal detector circuitry 22 may be transmitted to the external programmer device 38 to be stored and analyzed therein in more detail than is possible in the implanted device 10 itself. The receiver/transmitter 34 may also receive programming instructions from the external programmer device 38 for, for example, programming operating parameters of the implantable cardiac device 10. Communication between the receiver/transmitter 34 and the external programmer device 38 may be implemented in a conventional manner, e.g., via a telemetry (e.g., RF) link. It is noted that the external programmer device 38 is a relatively large and sophisticated device which is typically employed by a physician to monitor and control operation of the implantable device 10.

In accordance with the present invention, the implantable cardiac device 10 may also include a reed switch 40 mounted therein and coupled to the system processor 24. As will be discussed in more detail below, the reed switch 40 is operated (closed or opened) by the application of a magnetic field near the site of implantation in a patient of the implantable cardiac device 10. The system processor 24 detects the operation of the reed switch 40 as a patient activation request. In response to the patient activation request, the system processor 24 initiates a patient activation operation to provide an indication to the patient of atrial arrhythmia event status and atrial shock therapy availability, and to allow the patient to control the delivery of atrial shock therapy, as will be described in more detail below.

In accordance with the present invention, the implantable cardiac device 10 may preferably also include tone generation circuitry 42. The tone generation circuitry 42 may be implemented in a conventional manner, and is controlled by the system processor 24 to drive a small speaker 44 to produce different tones of sufficient volume to be audible by a patient in which the implantable device 10 is implanted. As will be discussed in more detail below, the tones produced by the tone generation circuitry 42 and speaker 44 may be used to indicate to a patient the status of an ongoing atrial arrhythmia event and the availability of atrial shock therapy.

The implantable cardiac device 10 also includes a battery 46, which provides power for the processor 24 and other circuit components of the implantable cardiac device 10.

The circuitry for implementing the signal detector 22, processor 24, cardioverter/defibrillator 32, receiver/transmitter 34, tone producer 42, and other functions of the implantable cardiac device 10 may be implemented in a conventional manner using analog or digital circuitry, including one or more microprocessors, or any combination thereof. As will be known to those skilled in the art, functions performed by the signal detector 22, cardioverter/defibrillator 32, receiver/transmitter 34, and tone producer 42, may be performed by independent analog and/or digital circuitry, as suggested by the illustration of FIG. 1, or may be implemented in one or more processors 24, or with a combination of independent circuits and one or more processors.

In accordance with the present invention, a patient in which the implantable cardiac device 10 is implanted may employ a patient activator communication device 12 to request an indication from the implanted cardiac device 10 of the status of atrial arrhythmia events detected by the implanted device 10 and the availability of atrial shock therapy, as well as to control the providing of atrial shock therapy by the implanted device 10. The patient activator 12 is preferably designed to be portable, and is preferably small in size and able to be held easily in the hand and manipulated by a patient. Various components which may be implemented in an activator 12 in accordance with the present invention are illustrated schematically in FIG. 2.

The activator 12 may preferably include a magnet 48 mounted therein. (In its simplest form, a patient activator 12 in accordance with the present invention may be implemented with a magnet 48 alone). When the patient activator 12 is positioned near the implant site of the implantable device 10 the magnetic field generated by the magnet 48 in the activator 12 operates the reed switch 40 coupled to the processor 24 in the implantable device 10. Operation of the reed switch 40 in this manner for at least a minimal period of time, e.g., one second, is recognized by the implanted device processor 24 as a patient activation request which initiates a patient-activation operation by the processor 24. During the patient-activation operation, the processor 24 employs a message generator function 30 to generate a status message which is provided to the patient to indicate the status of atrial arrhythmia events which are identified by the processor. Atrial arrhythmia event status messages may be provided to the patient, as described above, by controlling tone generation circuitry 42 in the implantable device 10 to generate a tone audible to the patient to indicate the status of an atrial arrhythmia event.

The atrial arrhythmia event status message generated by the implantable device 10 may also preferably be provided in a visual form to the patient, e.g., in a visual display provided on the patient activator 12. For example, the activator 12 may include tone detection circuitry 50. The tone detection circuitry 50 may be implemented in a conventional manner to detect the tones produced by the tone generation circuitry 42 in the implantable cardiac device 10 and to generate electrical signals in response thereto. The electrical signals generated by the tone detection circuitry 50 in the activator 12 are provided to an activator processor 52, which decodes the signals provided by the tone detection circuitry. The activator 12 also includes conventional display circuitry 54. The display circuitry 54 is driven by the activator processor 52, in response to the signals received from the tone detection circuitry 50, to provide a visual indication to the patient of the atrial arrhythmia event status indication provided by the implantable cardiac device 10. For example, the display circuitry 54 may include one or more LEDs or lamps 56 which are illuminated in a conventional manner to indicate, e.g., the receipt of a patient activation request by the implanted device 10, the presence or absence of an atrial arrhythmia event, the availability of atrial shock therapy, etc., as will be described in more detail below.

Figure 2:
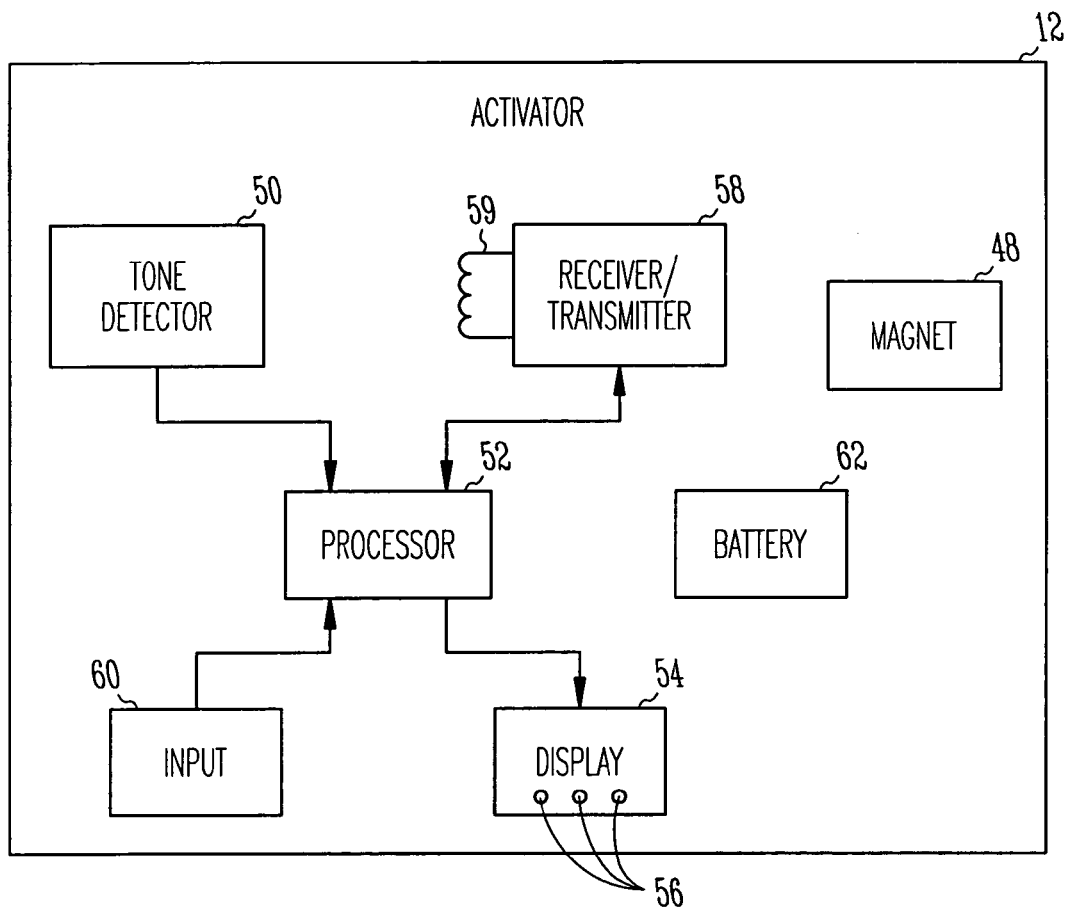
FIG. 2 is a more detailed schematic block diagram of an exemplary patient activator communication device in accordance with the present invention.

As an alternative to the magnet 48, for providing an activation request to the implanted cardiac device 10, and tone detector circuitry 50, for detecting atrial arrhythmia event status indication messages provided by the implanted device 10, the activator 12 may include conventional receiver/transmitter circuitry 58, including an antenna 59. The activator receiver/transmitter 58 may be implemented in a conventional manner, and may be coupled to the receiver/transmitter 34 (or another similar circuit) in the implanted device 10, via a telemetry (e.g., RF) link, to both provide patient activation request signals to and receive status information from the implanted cardiac device 10. The activator receiver/transmitter 58 is coupled to, and controlled by, the activator processor 52. Patient input circuitry 60 is preferably also provided in the activator 12 and coupled to the activator processor 52. The activator input circuitry 60 may include conventional buttons, switches, dials, etc., and related electronic circuitry. A patient employs the activator input circuitry 60 to initiate a patient activation operation in the implanted device 10. For example, the patient may push a button on the activator 12, which is part of the input circuitry 60, to request the status of an ongoing atrial arrhythmia. A signal generated by the activator input circuitry 60 is received by the processor 52 which, in turn, generates a command signal requesting, e.g., an updated atrial arrhythmia status indication from the implanted device 10. This command message is, in turn, provided to the activator receiver/transmitter 58, to be transmitted to the implanted device 10, e.g., via the receiver/transmitter 34 therein, over the telemetry link. The received command signal is, in turn, processed by the implanted device processor 24. In response to the request, a message indicating, e.g., atrial arrhythmia event status, is generated by the implanted device processor 24, and provided to the implanted device receiver/transmitter 34 for transmission back to the activator 12. The status message is received by the activator receiver/transmitter 58 and provided to the activator processor 52. The activator processor 52 processes the atrial arrhythmia status indication message received from the implanted device 10, and generates therefrom an indication of ongoing atrial arrhythmia status, which, e.g., may be presented to the patient by controlling the activator display 54. Of course, the indication may be provided visually, audibly, and/or in any other manner to a patient on the activator 12. Other status information, such as shock therapy availability, may also be requested from the implanted device 10 using the input 60 and receiver/transmitter circuitry 58. Such telemetry circuitry may also be employed to request or withhold the providing of shock therapy by the implanted device 10. It should be noted that a patient activator 12 will typically include either the receiver/transmitter 58 and input circuitry 60 or a magnet 48 and tone detector 50, but may include both systems, as illustrated in FIG. 2.

An exemplary process in accordance with the present invention for providing patient control and monitoring of atrial shock therapy provided by an implanted cardiac device 10 will now be described in detail with reference to the exemplary flowchart diagram of FIG. 3. In accordance with the present invention, the implanted device 10 may determine automatically at 64 the presence or absence of an atrial arrhythmia, e.g., atrial tachycardia, fibrillation, or flutter, without a specific request to do so from external to the patient. For example, conventional methods may be used by the implanted device processor 24 to monitor ventricular and/or atrial activity detected by the signal detector 22 to determine the likelihood of the occurrence of an atrial arrhythmia. If conditions indicate that an atrial arrhythmia is likely, the processor 24 may employ one or more conventional atrial arrhythmia detection algorithms 28 to determine if an atrial arrhythmia is occurring, and the nature of the arrhythmia.

The implanted device processor 24 also continually checks for the receipt of an activation request from the patient activator 12 at 66. As described above, such a request may be provided by a magnet 48 in the activator 12 positioned near the implanted device 10, to operate the reed switch 40, which, in turn, is detected by the processor 24. Alternatively, an activation request signal may be sent to the implanted device processor 24 via a telemetry link established between the activator receiver/transmitter 58 and the implanted device receiver/transmitter 34. If an activation request 66 is not detected by the implanted device processor 24, the processor 24 continues to monitor the status of a detected atrial arrhythmia 64, continually updating ongoing atrial arrhythmia status, while continually checking for receipt of an activation request 66, until such a request is received.

If an activation request 66 is received by the implanted device processor 24, the processor 24 generates a confirmation message or signal at 68, e.g., employing the message generator function 30 stored in memory 26, to provide confirmation to a patient that the activation request has been received by the implanted device 10. The confirmation signal or message may be in the form of a message transmitted from the implanted device receiver/transmitter 34 to the activator receiver/transmitter 58 and displayed or otherwise presented on the activator 12 by the activator processor 52, e.g., on the activator display 54. Alternatively, the confirmation signal may be provided as a tone produced by the tone producer 42 and speaker 44 in the implanted device 10 and audible by the patient, and/or received by the tone detector 50 in the activator 12 and translated to a visual signal displayed on the activator display 54.

The implanted device processor 24 then determines the current updated status 70 of any atrial arrhythmia which may be occurring in the patient's heart 20 and which has been detected by the implanted device 10. If an atrial arrhythmia is occurring, the current status of the atrial arrhythmia is indicated to the patient at 72. If no arrhythmia is occurring, this fact may also be indicated at 74, or simply no positive indication of atrial arrhythmia is provided. The indication of the current status of an atrial arrhythmia may be generated by the implanted device processor 24 employing the message generator function 30. The message indicating the status of an ongoing atrial arrhythmia may be provided via the implanted device receiver/transmitter 34 and activator receiver/transmitter 58 to the activator 12 for display or other presentation thereon. Alternatively, the status of an ongoing atrial arrhythmia may be provided as an audible tone generated by the implanted device tone producer circuitry 42 and speaker 44, and audible to the patient and/or received by the activator tone detector 50 and translated into a visual display on the activator 12.

After providing an indication to a patient of the current ongoing status of an atrial arrhythmia, the processor 24 may return to monitoring and updating the status of the atrial arrhythmia 64 and waiting for a subsequent activation request 66 from the activator 12. As long as an activation request 66 is active, e.g., as long as the patient activator 12 is in position to operate the reed switch 40, the implanted device processor 24 may provide automatically periodically updated atrial arrhythmia status indications to the patient in the manner described. Such updated status indications may be provided automatically, as long as the activation request 66 is active, at each occurrence of a selected cardiac event, e.g., a ventricular event.

The implanted device processor 24 may also determine whether atrial shock therapy is available at 76, and provide an indication of atrial shock therapy availability to the patient at 78 and 80, e.g., in the form of a message transmitted from the implanted device 10 to the activator 12 via a telemetry link, and/or as an audible tone. For example, shock therapy may be indicated as available if several predetermined conditions are satisfied. Such conditions may include, for example, the presence of an ongoing atrial arrhythmia, the programming ON of shock therapy by a physician (using the programmer 38), the fact that shock therapy had not just been attempted for the ongoing atrial arrhythmia event, and the satisfaction of one or more verification conditions, such as a detected atrial rate exceeding the detected ventricular rate, thereby confirming an atrial only arrhythmia. Other conditions for determining whether or not shock therapy is available may, of course, also be employed.

Figure 3:
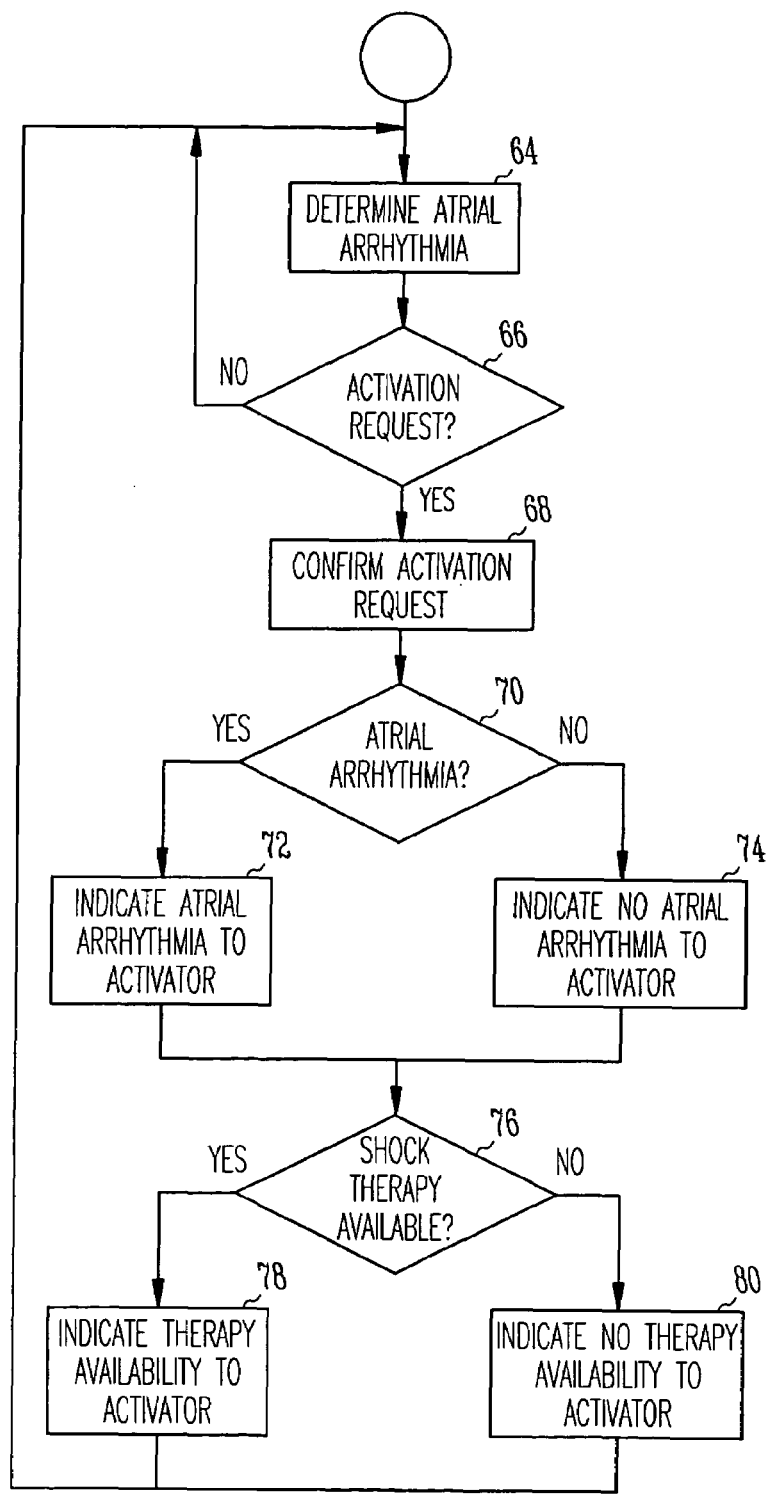
FIG. 3 is flowchart diagram illustrating an exemplary method for obtaining updated atrial arrhythmia event status information from an implanted cardiac device in accordance with the present invention using a patient activator communication device in accordance with the present invention.

It should be understood that not all of the steps illustrated schematically in FIG. 3 need be performed, and the steps illustrated may be performed in a different order, in accordance with the present invention. For example, the steps of confirming an activation request 68, indicating the presence or absence of an atrial arrhythmia 72, 74, and indicating the availability of shock therapy 78, 80 may be performed essentially simultaneously. These three pieces of information may be provided to a patient using a minimal number of three distinctively different tones produced by the tone producer 42 and speaker 44. A first tone may indicate that there is no ongoing atrial arrhythmia (and thus that atrial shock therapy is not available). A second tone may indicate that there is an ongoing atrial arrhythmia, but that atrial shock therapy is not available. A third tone may indicate that there is an ongoing atrial arrhythmia, and that atrial shock therapy is available. The production of any tone by the implanted device 10 confirms that an activation request has been received thereby from the activator 12.

An important feature of the present invention, as illustrated in FIG. 3, is that the determination of the status of an atrial arrhythmia by the implanted device processor 24 is performed automatically by the processor 24 independently of the receipt of an activation request from a patient. As along as an atrial arrhythmia is ongoing, the processor 24 continues to monitor and update the status of the atrial arrhythmia periodically, e.g., at each occurrence of a selected cardiac, e.g., ventricular, event. Thus, the current status of an ongoing atrial arrhythmia is readily available to be presented to a patient on request using the activator 12. Reinitiation of atrial arrhythmia detection by the implanted device processor 24 is not required each time the patient requests an atrial arrhythmia status indication update.

A patient informed as to the ongoing status of an atrial arrhythmia using a system and method in accordance with the present invention preferably is able to employ such information to control the operation of the implanted device 10 to provide atrial shock therapy. For example, a patient may feel the onset of what he may believe to be an atrial arrhythmia. By use of the activator device 12, the patient is able to confirm whether or not an atrial arrhythmia is occurring. The activator 12 may then also be employed to request the implanted device 10 to proceed with providing atrial shock therapy to terminate the atrial arrhythmia (if such shock therapy is indicated as being available), or to withhold the providing of such therapy by the implanted device 10. For example, a patient may wish to withhold immediate atrial shock therapy until the patient is better prepared for the therapy, at which point the activator device 12 may be employed to initiate a shock therapy request.

Patient controlled requesting and withholding of atrial shock therapy may be initiated by a patient using the activator input circuitry 60. The proper command signal may then be transmitted to the implanted device 10 over the telemetry link between activator receiver/transmitter 58 and implanted device receiver/transmitter 34. Alternatively, the requesting and withholding of shock therapy may be performed using a more simple activator device 12 including a magnet 48. For example, as discussed above, by positioning the activator magnet 48 near the implanted device 10, to operate the reed switch 40, a patient activation operation is initiated in the implanted device 10. If the activation request is thus presented to the implanted device 10 for less than a threshold duration (e.g., less than seven seconds), the patient may thereby instruct the implanted device processor 24 to withhold the providing of atrial shock therapy. If the activator 12 is maintained in position for longer than the threshold duration (e.g., greater than seven seconds), the implanted device processor 24 may be instructed to proceed with providing atrial shock therapy, either immediately or once the activator 12 is removed from position near the implanted device 10. Any shock therapy initiated in the implanted device 10 may be disabled by maintaining the activator 12 in position for at least a stop therapy threshold duration, which may be much longer than the threshold duration required to initiate therapy. For example, any shock therapy initiated in the implanted device 10 may be disabled if the activator 12 is maintained in position for longer than a stop therapy threshold duration of, e.g., sixty seconds. Shock therapy may be reinitiated following such a stop therapy operation by removing the activator 12 from position near the implanted device 10 and then replacing the activator 12 in position near the implanted device 10 for at least the initial duration required to re-initiate a patient activation operation. (Preferably, all atrial shock therapy is disabled during application of the activator magnet 48 near the implanted device 10.)

Of course, as discussed above, by positioning the activator magnet 48 near the implanted device 10, the patient also requests an indication of the ongoing status of an atrial arrhythmia. Thus, a simple activator device 12 employing a magnet 48 may be used both to request an atrial arrhythmia status indication from an implanted device 10 in accordance with the present invention (by the presence of the thus generated activation signal), as well as to control the operation of the implanted device 10 to provide atrial shock therapy (by the duration of the presence of the thus generated activation signal). Since relatively complicated activator receiver/transmitter 58, input 60, and other circuitry are not required, a relatively inexpensive and simple to operate activator device 12 may thus be employed in accordance with the present invention to both monitor the status of an ongoing atrial arrhythmia and to control the providing of atrial shock therapy to treat the arrhythmia.

It is understood that the present invention is not limited to the particular exemplary embodiments and applications thereof illustrated and described herein, but embraces such modified forms thereof as come within the scope of the following claims.

What is claimed is:

1. A patient controllable atrial shock therapy system, comprising:
    an implantable device including:
        means for detecting an atrial arrhythmia event episode and updating automatically an atrial arrhythmia event status periodically throughout the duration of a detected atrial arrhythmia event episode;
        means for detecting a patient activation request originating from external to the implantable device; and
        means for generating a message indicating to a patient the periodically updated ongoing atrial arrhythmia event status in response to detection of the patient activation request.

2. The patient controllable atrial shock therapy system of claim 1 wherein the means for detecting the atrial arrhythmia event episode and updating automatically the atrial arrhythmia event status includes means for detecting atrial arrhythmia event episodes selected from the group of atrial arrhythmias consisting of atrial tachycardia and atrial fibrillation.

3. The patient controllable atrial shock therapy system of claim 1 wherein the means for detecting the atrial arrhythmia event episode and updating automatically the atrial arrhythmia event status includes means for updating atrial arrhythmia event status periodically at each occurrence of a selected cardiac event occurring throughout the duration of a detected atrial arrhythmia event episode.

4. The patient controllable atrial shock therapy system of claim 3 wherein the means for detecting the atrial arrhythmia event episode and updating automatically the atrial arrhythmia event status includes means for updating atrial arrhythmia event status periodically at each occurrence of a ventricular event occurring throughout the duration of a detected atrial arrhythmia event episode.

5. The patient controllable atrial shock therapy system of claim 1 wherein the means for detecting the patient activation request includes a reed switch responsive to a magnetic field to operate the reed switch to provide the patient activation request.

6. The patient controllable atrial shock therapy system of claim 5 wherein the means for generating the message generates messages indicating the periodically updated arrhythmia event status as long as the magnetic field operates the reed switch.

7. The patient controllable atrial shock therapy system of claim 1 wherein the means for generating the message includes means for generating messages indicating the periodically updated arrhythmia event status as long as the patient activation request is detected.

8. The patient controllable atrial shock therapy system of claim 1 wherein the means for generating the message includes means for generating an audible tone indicating the periodically updated arrhythmia event status.

9. The patient controllable atrial shock therapy system of claim 1 wherein the means for detecting the patient activation request includes a reed switch responsive to a magnetic field to operate the reed switch to provide the patient activation request, wherein the means for generating the message generates the message indicating the periodically updated arrhythmia event status in response to operation of the reed switch, and wherein the means for generating the message includes means for generating an audible tone indicating the periodically updated arrhythmia event status, and further comprising a hand-held activator including:
    a magnet for generating the magnetic field to operate the reed switch when the activator is positioned near the implantable device;
    means for receiving the audible tone indicating the periodically updated arrhythmia event status and converting the audible tone indicating the periodically updated arrhythmia event status into an electrical signal indicating the periodically updated arrhythmia event status; and
    means responsive to the electrical signal indicating the periodically updated arrhythmia event status for displaying on the activator a visual indication of the periodically updated arrhythmia event status.

10. The patient controllable atrial shock therapy system of claim 1 wherein the means for detecting the patient activation request includes a patient activation request receiver adapted to receive a patient activation request signal, wherein the implantable device comprises additionally a status message transmitter responsive to the means for generating the message for transmitting a status message indicating the periodically updated arrhythmia event status, and further comprising a hand-held activator including:
- a patient activation request transmitter for transmitting a patient activation request signal to be received by the patient activation request receiver;
- a status message receiver adapted to receive the status message indicating the periodically updated arrhythmia event status from the status message transmitter; and
- means responsive to the status message received by the status message receiver for displaying on the activator a visual indication of the periodically updated arrhythmia event status.

11. A patient controllable cardiac shock therapy system, comprising:
an implantable device including:
- means for detecting a cardiac arrhythmia and providing a cardiac arrhythmia event status;
- means for detecting a patient activation request originating from external to the implantable device; and
- means for generating audible tone messages within the implantable device indicating the cardiac arrhythmia event status in response to detection of the patient activation request.

12. The patient controllable cardiac shock therapy system of claim 11 further comprising an external activator creating a magnetic field representative of the patient activation request, and wherein the means for detecting the patient activation request detects the magnetic field.

13. The patient controllable cardiac shock therapy system of claim 12 wherein the means for detecting the patient activation request comprises a reed switch operating in response to the magnetic field.

14. The patient controllable cardiac shock therapy system of claim 11 further comprising an external activator including an activator receiver/transmitter to transmit the patient activation request, and wherein the means for detecting the patient activation request comprises an implantable device receiver/transmitter to receive the patient activation request.

15. A system comprising:
an implantable device including:
- an arrhythmia detector to detect an arrhythmia event episode and provide an arrhythmia event status during the detected arrhythmia event episode;
- a switch operating in response to a magnetic field representative of an external activation request; and
- an implantable device processor coupled to the switch to detect the external activation request, the implantable device processor generating a message indicative of the arrhythmia event status in response to the external activation request; and
a patient controlled hand-held external activator adapted to provide the magnetic field representative of the external activation request.

16. The system of claim 15 wherein the arrhythmia detector comprises an atrial arrhythmia detector.

17. The system of claim 15 wherein the switch comprises a reed switch, and wherein the external activator comprises a magnet generating the magnetic field representative of the external activation request.

18. The system of claim 17 wherein the implantable device further comprises a tone producer coupled to the implantable device processor, the tone producer adapted to generate an tone indicative of the arrhythmia event status.

19. The system of claim 18 wherein the implantable device further comprises a speaker coupled to the tone producer.

20. The system of claim 18 wherein the external activator further comprises:
- a tone detector adapted to detect the tone; and
- an activator processor coupled to the tone detector, the activator processor adapted to decode the detected tone.

21. The system of claim 18 wherein the external activator further comprises a display, coupled to the activator processor, to provide a visual indication of the arrhythmia event status.

* * * * *

UNITED STATES PATENT AND TRADEMARK OFFICE
CERTIFICATE OF CORRECTION

PATENT NO. : 6,980,857 B2
DATED : December 27, 2005
INVENTOR(S) : Chen et al.

It is certified that error appears in the above-identified patent and that said Letters Patent is hereby corrected as shown below:

<u>Title page,</u>
Item [56], References Cited, U.S. PATENT DOCUMENTS, after "9/2003" delete "Favet et al." and insert -- Chen et al. --.

Signed and Sealed this

Thirtieth Day of May, 2006

JON W. DUDAS
*Director of the United States Patent and Trademark Office*